(12) United States Patent
Ito et al.

(10) Patent No.: US 6,617,353 B1
(45) Date of Patent: Sep. 9, 2003

(54) PREPARATION FOR NASAL ADMINISTRATION

(75) Inventors: Shusei Ito, Tokyo (JP); Kenji Yamada, Tokyo (JP); Ayumi Koda, Tokyo (JP); Mari Nakano, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/762,485

(22) PCT Filed: Nov. 22, 2000

(86) PCT No.: PCT/JP00/08239

§ 371 (c)(1),
(2), (4) Date: Feb. 7, 2001

(87) PCT Pub. No.: WO01/37839

PCT Pub. Date: May 31, 2001

(30) Foreign Application Priority Data

Nov. 24, 1999 (JP) .............................................. 11-333281

(51) Int. Cl.⁷ ........................ A01N 37/00; A01N 37/08; A61K 31/19
(52) U.S. Cl. ........................................ 514/557; 514/572
(58) Field of Search ............................ 424/43; 514/557, 514/572

(56) References Cited

U.S. PATENT DOCUMENTS

| 5,234,953 A | 8/1993 | Crow et al. ................. 514/573 |
| 5,545,666 A | 8/1996 | Sato et al. ................... 514/530 |

FOREIGN PATENT DOCUMENTS

| EP | 0 737 676 A1 | 10/1996 | |
| EP | 737676 | 10/1996 | |
| JP | 7-233144 | 9/1995 | ......... C07C/405/00 |
| JP | 7-242622 A | 9/1995 | |
| JP | 8-208599 A | 8/1996 | |
| JP | 11-130660 | 5/1999 | |
| JP | 2000-273082 A | 10/1999 | |
| WO | 99/61029 | 12/1999 | ......... A61K/31/557 |

OTHER PUBLICATIONS

Patent Abstracts of Japan 07–233144, Sep. 05, 1995.

*Primary Examiner*—Alton N. Pryor
(74) *Attorney, Agent, or Firm*—Sughrue Mion, PLLC

(57) ABSTRACT

A preparation for nasal administration which comprises as an effective ingredient a prostaglandin derivative represented by Formula (I):

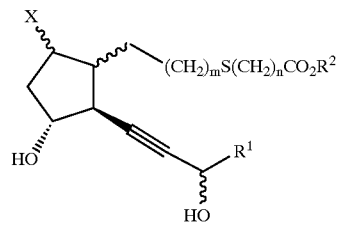

wherein X is a halogen atom, $R^1$ is a $C_{3-10}$ cycloalkyl group, a $C_{3-10}$ cycloalkyl group substituted with $C_{1-4}$ alkyl group(s) or a $C_{4-13}$ cycloalkylalkyl group, $R^2$ is a hydrogen atom, a $C_{1-10}$ alkyl group or a $C_{3-10}$ cycloalkyl group, m is an integer of 0 to 3, and n is an integer of 1 to 4 or a pharmaceutically acceptable salt thereof and a water-soluble polymer.

16 Claims, No Drawings

PREPARATION FOR NASAL ADMINISTRATION

This Application is a 371 of PCT/JP00/08239 filed Nov. 22, 2000.

TECHNICAL FIELD

The present invention relates to a preparation for nasal administration comprising a prostaglandin derivative as an effective ingredient.

BACKGROUND ART

Since prostaglandin (hereinafter referred to as "PG") exhibits various important pharmacological and physiological actions in a trace amount, the syntheses of a great number of derivatives from natural PGs and the biological activities have been investigated with the intention of a practical use as medicines. Particularly, many compounds which have a triple bond between the 13- and 14-positions were synthesized by Sato et al, and among of these compounds are PG derivatives described in Japanese Patent Kokai Hei 7-233144.

The PG derivatives in the above-mentioned gazette are described to have an excellent lowering action of ocular tension and be able to be used as eye drops or an eye ointment. However, there have not been known a preparation for nasal administration comprising said prostaglandin derivatives or its sleep-inducing effect.

DISCLOSURE OF THE INVENTION

As a result of the extensive studies to solve the above purpose, the present inventors have found that the following prostaglandin derivatives, when combined with a certain polymer, have an excellent sleep-inducing effect by nasal administration, and thereby the present invention has been accomplished.

That is, an aspect of the present invention is to provide a preparation for nasal administration (hereinafter referred to as "preparation of the present invention" or "preparation of the present applications") which comprises as an effective ingredient a prostaglandin derivative represented by Formula (I):

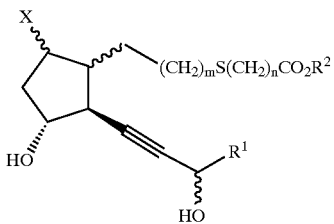

wherein X is a halogen atom, $R^1$ is a $C_{3-10}$ cycloalkyl group, a $C_{3-10}$ cycloalkyl group substituted with $C_{1-4}$ alkyl group(s) or a $C_{4-13}$ cycloalkylalkyl group, $R^2$ is a hydrogen atom, a $C_{1-10}$ alkyl group or a $C_{3-10}$ cycloalkyl group, m is an integer of 0 to 3, n is an integer of 1 to 4, and a wavy line is a bond which may be in the R or S-configuration, or a pharmaceutically acceptable salt thereof and a water-soluble polymer.

A further aspect of the present invention is to provide a preparation for nasal administration which comprises as an effective ingredient a prostaglandin derivative represented by Formula (A):

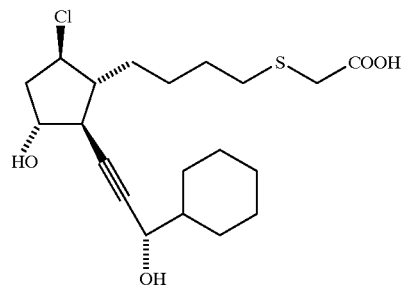

or a pharmaceutically acceptable salt thereof and a water-soluble polymer.

A still further aspect of the present invention is to provide the above-mentioned preparation for nasal administration wherein the water-soluble polymer is at least one member selected from the group consisting of a bridged vinyl polymer and a water-soluble cellulose ether.

A still further aspect of the present invention is to provide the above-mentioned preparation for nasal administration wherein the water-soluble polymer is at least one member selected from the group consisting of hydroxypropyl cellulose, hydroxypropylmethyl cellulose, polyvinylpyrrolidone and methyl cellulose.

A still further aspect of the present invention is to provide the above-mentioned preparation for nasal administration wherein the water-soluble polymer is hydroxypropyl cellulose.

A still further aspect of the present invention is to provide the above-mentioned preparation for nasal administration wherein the water-soluble polymer carries the prostaglandin derivative represented by Formula (I) or (A) or the pharmaceutically acceptable salt thereof.

A still further aspect of the present invention is to provide the above-mentioned preparation for nasal administration wherein the prostaglandin derivative represented by Formula (I) or (A) or the pharmaceutically acceptable salt thereof adheres to the water-soluble polymer and/or disperses in the water-soluble polymer.

A still further aspect of the present invention is to provide the above-mentioned preparation for nasal administration wherein a coating layer comprising the prostaglandin derivative represented by Formula (I) or (A) or the pharmaceutically acceptable salt thereof as an effective ingredient dispersed in the water-soluble polymer adheres to the surface of the water-soluble polymer for carrying the effective ingredient.

A still further aspect of the present invention is to provide the above-mentioned preparation for nasal administration which is a sleep-inducing preparation.

A still further aspect of the present invention is to provide a kit of a preparation for nasal administration which comprises the above-mentioned sleep-inducing preparation and a device for administration thereof.

A still further aspect of the present invention is to provide a method for sleep-inducing which comprises administering nasally a pharmaceutically effective amount of the above-mentioned sleep-inducing preparation to a human.

The compounds of Formula (I) to be used in the present invention are illustrated in more detail as follows.

General preparation methods of the compound of Formula (I)

The compound of Formula (I) can be prepared according to the following reaction formulae.

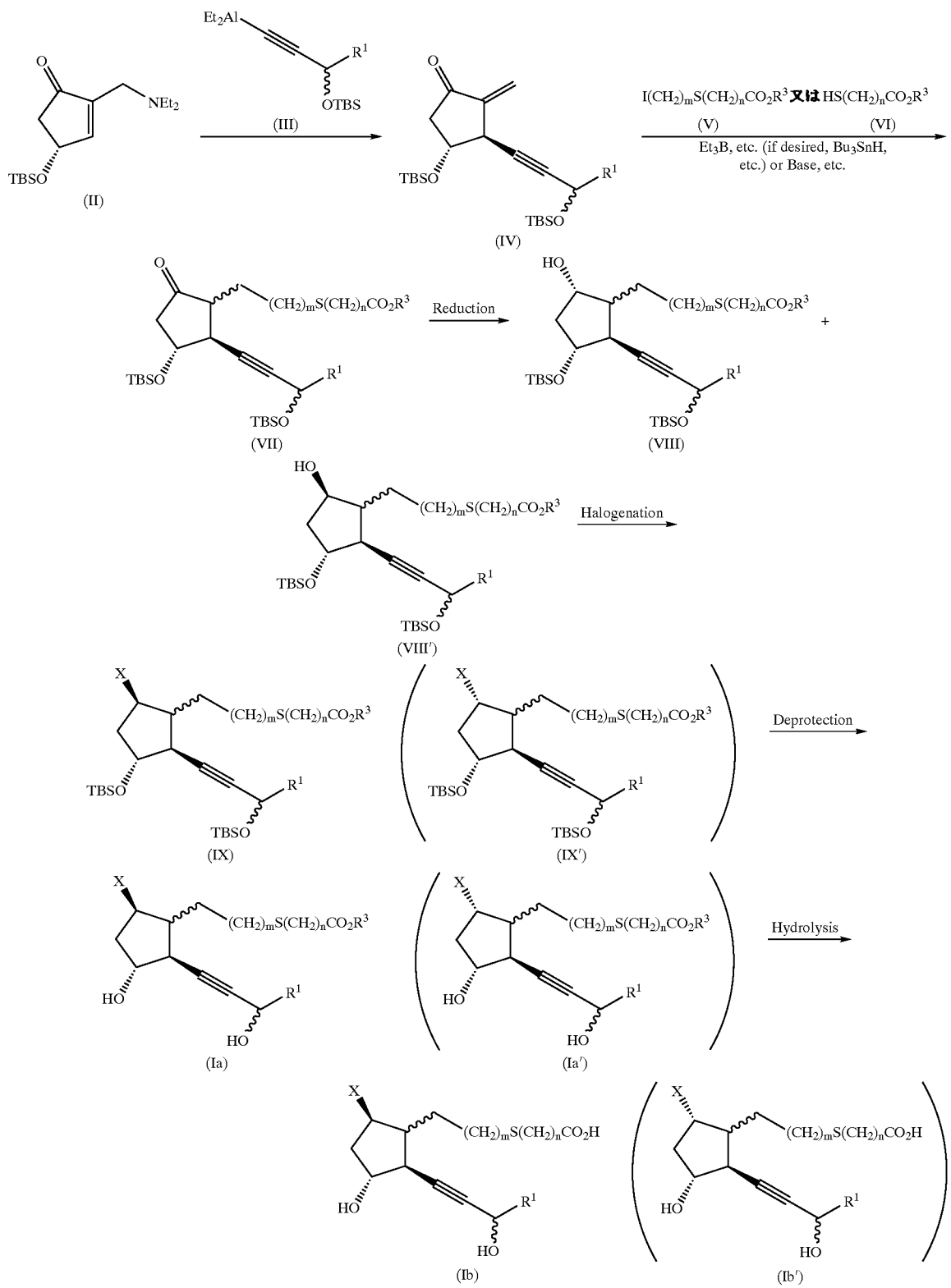

In the reaction formulae, $R^3$ is a $C_{1-10}$ alkyl group or a $C_{3-10}$ cycloalkyl group, TBS is a tert-butyldimethylsilyl group, and X, $R^1$, m and n are as defined above).

The above-mentioned reaction formulae are illustrated as follows.

(1) At first, a known compound of Formula (II) is reacted with 0.8 to 2.0 equivalents of an organic aluminum compound represented by Formula (III) in an inert solvent (e.g. benzene, toluene, tetrahydrofuran, diethyl ether, methylene chloride or n-hexane) at −10 to 30° C., preferably 0 to 10°

C., according to the method of Sato et al. (Journal of Organic Chemistry, vol. 53, page 5590 (1988)) to stereospecifically give a compound of Formula (IV).

(2) The compound of Formula (IV) is reacted with 0.5 to 4 equivalents of a compound represented by Formula (V) or (VI) and 0.05 to 2 equivalents of a radical generator (e.g. azobisisobutyronitrile, azobiscyclohexane carbonitrile, benzoyl peroxide or triethylborane) and, if desired, using 1 to 5 equivalents of a radical reductant (e.g. tributyltin hydride, triphenyltin hydride, dibutyltin hydride or diphenyltin hydride) in an inert solvent (e.g. benzene, toluene, xylene, n-hexane, n-pentane or acetone) at −78 to 100° C., thereby a compound of Formula (VII) is obtained.

Alternatively, the compound of Formula (IV) is reacted with 0.5 to 4 equivalents of a compound represented by Formula (V) or (VI) using 0.05 to 2 equivalents of a base such as organic amines (e.g. triethylamine, diisopropylamine, pyridine or dimethylaniline) or basic resins (e.g. polyvinylpolypyrrolidone, diisopropylaminomethyl-polystylene or (piperidinomethyl) polystylene) in an inert solvent (e.g. benzene, toluene, xylene, n-hexane, n-pentane or acetone) at −78 to 100° C., thereby a compound of Formula (VII) can be obtained.

(3) The compound of Formula (VII) is reduced with 0.5 to 5 equivalents of a reductant (e.g. potassium borohydride, sodium borohydride, lithium tricyanoborohydride, lithium tri-sec-butyl borohydride or aluminum diisobutyl hydride-BHT (2,6-di-tert-butyl-p-cresol) in an organic solvent (e.g. tetrahydrofuran, diethyl ether, ethyl alcohol, methyl alcohol or toluene) at −78 to 40° C. to give compounds of Formulae (VIII) and (VIII'). These compounds of Formulae (VIII) and (VIII') can be purified by a conventional separation method such as a column chromatography.

(4) The compound of Formula (VIII) or (VIII') is mesylated or tosylated, for example, with 1 to 6 equivalents of methanesulfonyl chloride or p-toluenesulfonyl chloride in the presence of a base (e.g. triethylamine, pyridine or 4-dimethylaminopyridine) in a suitable solvent (e.g. pyridine or toluene) at −20 to 40° C., followed by chlorination with 1 to 16 equivalents of tetra-n-butylammonium chloride to give a compound of Formula (IX) or (IX') wherein X is a chlorine atom. Herein, bromination or fluorination can be also carried out in an ordinary manner. For example, bromination can be carried out by a reaction with 1 to 10 equivalents of carbon tetrabromide in the presence of 1 to 10 equivalents of triphenylphosphine and 1 to 10 equivalents of pyridine in acetonitrile, and fluorination can be carried out by a reaction with 5 to 20 equivalents of diethylaminosulfur trifluoride (DAST) in methylene chloride.

(5) The protective group of the hydroxyl group of the compound of Formula (IX) or (IX'), i.e. a tert-butyldimethylsilyl group is removed by using hydrofluoric acid, pyridinium poly(hydrogenfluoride) or hydrochloric acid under conventional conditions in a solvent (e.g. methanol, ethanol, acetonitrile, a mixture thereof or a mixture of these solvents and water) to give a PG derivative of Formula (Ia) or (Ia') relating to the present invention, i.e. a compound of Formula (I) wherein $R^2$ is a $C_{1-10}$ alkyl group or a $C_{3-10}$ cycloalkyl group.

(6) The compound of Formula (Ia) or (Ia') is hydrolyzed using 1 to 6 equivalents of a base in a conventional solvent for hydrolysis to give a PG derivative of Formula (Ib) or (Ib') relating to the present invention, i.e. a compound of Formula (I) wherein $R^2$ is a hydrogen atom. Examples of the base to be used herein are lithium hydroxide and potassium carbonate, and examples of the solvent are acetonitrile, acetone, methanol, ethanol, water and a mixture thereof.

Furthermore, the compound of Formula (Ia) is hydrolyzed by a reaction with an enzyme in a buffer solution such as phosphate buffer or tris-hydrochloride buffer, if necessary, by using an organic solvent (e.g. a water-miscible solvent such as acetone, methanol or ethanol) to give the PG derivative of the present invention, i.e. the compound of Formula (Ib). Examples of the enzyme to be used herein are enzymes produced by microorganisms (e.g. enzymes produced by microorganisms belonging to Candida sp. or Pseudomonas sp.) and enzymes prepared from animal organs (e.g. enzymes prepared from pig liver or pig pancreas). Commercially available enzymes are, for example, lipase VII (derived from microorganism of Candida sp.; Sigma Co.), lipase AY (derived from microorganism of Candida sp.; Amano Pharmaceutical Co.), lipase PS (derived from microorganism of Pseudomonas sp.; Amano Pharmaceutical Co.), lipase MF (derived from microorganism of Pseudomonas sp.; Amano Pharmaceutical Co.), PLE (prepared from pig liver; Sigma Co.), lipase II (prepared from pig pancreas; Sigma Co.) or lipoprotein lipase (prepared from pig pancreas; Tokyo Kasei Kogyo Co.).

The amount of the enzyme to be used, while depending on the potency of the enzyme and the amount of the substrate (the compound of Formula (Ia)), is usually 0.1 to 20 parts by weight based on the substrate, and the reaction temperature is from 25 to 50° C., preferably 30 to 40° C.

The definitions of the substituents in the compounds of Formula (I) of the present invention are illustrated in more detail as follows.

The "halogen atom" as defined for X refers to a fluorine atom, a chlorine atom, a bromine atom or an iodine atom, and X is preferably a chlorine atom or a bromine atom, and especially preferably a chlorine atom.

The definitions for $R^1$ are illustrated as follows.

Examples of the "$C_{3-10}$ cycloalkyl group", either by itself or as a part of the "$C_{3-10}$ cycloalkyl group substituted with $C_{1-4}$ alkyl group(s)" are a cyclopropyl group, a cyclobutyl group, a cyclopentyl group, a cyclohexyl group and a cycloheptyl group.

The "$C_{1-4}$ alkyl group" as a part of the "$C_{3-10}$ cycloalkyl group substituted with $C_{1-4}$ alkyl group(s)" refers to a straight or branched alkyl group, and examples thereof are a methyl group, an ethyl group, a propyl group, an isopropyl group, a butyl group, an isobutyl group and a tert-butyl group.

Examples of the "$C_{3-10}$ cycloalkyl group substituted with $C_{1-4}$ alkyl group(s)" are a methylcyclopropyl group, a methylcyclohexyl group and an ethylcyclohexyl group.

Examples of the "$C_{4-13}$ cycloalkylalkyl group" are a cyclopropylmethyl group, a cyclobutylmethyl group, a cyclopentylmethyl group, a cyclopentylethyl group, a cyclohexylmethyl group, a cyclohexylethyl group and a cycloheptylmethyl group.

$R^1$ is preferably a $C_{5-7}$ cycloalkyl group, and especially preferably a cyclohexyl group.

The "$C_{1-10}$ alkyl group" as defined for $R^2$ refers to a straight or branched alkyl group, and examples thereof are a methyl group, an ethyl group, a propyl group, an isopropyl group, a butyl group, an isobutyl group, a tert-butyl group, a pentyl group, an isopentyl group, a 2-ethylpropyl group, a hexyl group, an isohexyl group, a 1-ethylbutyl group, a heptyl group, an isoheptyl group, an octyl group, a nonyl group and a decyl group.

Preferably, $R^2$ is a hydrogen atom or a methyl group.

With regard to a preferable combination of m and n, m is 3 when n is 1, or m is 0 when n is 4.

Examples of the "pharmaceutically acceptable salt" are salts with an alkali metal (e.g. sodium or potassium), an alkali earth metal (e.g. calcium or magnesium), ammonia, methylamine, dimethylamine, cyclopentylamine, benzylamine, piperidine, monoethanolamine, diethanolamine, monomethylmonoethanolamine, tromethamine, lysine, a tetraalkyl ammonium and tris (hydroxymethyl)aminomethane.

The "water-soluble polymer" as used in the present invention refers to a polymer which is soluble in water, and examples thereof are at least one member selected from the group consisting of a bridged vinyl polymer and a water-soluble cellulose ether.

The "bridged vinyl polymer" includes a bridged polyvinyl alcohol (e.g. polyvinyl alcohol), a bridged polyacrylic acid or salts thereof (e.g. polyacrylamide) or polyvinylpyrrolidone.

The "water-soluble cellulose ether" includes hydroxypropyl cellulose, a hydroxyalkylmethyl cellulose (e.g. hydroxypropylmethyl cellulose), methyl cellulose, hydroxyethyl cellulose, ethylhydroxyethyl cellulose, carboxymethylhydroxyethyl cellulose, carboxymethyl cellulose sodium or cationic cellulose ether.

In view of the simple production and effectiveness of the preparation for nasal administration, preferable examples of the water-soluble polymer to be used are at least one member selected from the group consisting of hydroxypropyl cellulose, hydroxypropylmethyl cellulose, polyvinylpyrrolidone and methyl cellulose. Hydroxypropyl cellulose is especially preferably used.

The water-soluble polymer to be used herein includes various commercially available or synthesized ones of which solubility, substitution degree (i.e. viscosity) or particle size may be different, and they can be arbitrarily by chosen as long as having a purity usable for a pharmaceutical preparation.

The "water-soluble polymer carries the prostaglandin derivative of Formula (I) or (A) or the pharmaceutically acceptable salt thereof" refers to a state in which the prostaglandin or the pharmaceutically acceptable salt thereof (hereinafter optionally referred to as "drug") is carried by the water-soluble polymer so as to be absorbed at the site of the drug absorption. Here, the water-soluble polymer which carries the drug is referred to as "carrier".

In view of the drug transition to the brain, the particle size of the water-soluble polymer carrier is preferably about 20 to about 250 μm, especially preferably about 75 to about 250 μm.

In the present invention, the "dispersion of the drug in the water-soluble polymer" refers to a state wherein the drug exists in the form of monomolecule in the water-soluble polymer. Preferably, the greater part of the drug exists in a solid-dispersion state (the drug is amorphous).

The dispersion state of the drug can be produced by an ordinary method such as, for example, a fusion method, a solvent method, a fusion-solvent method or a mechanochemical method.

Referring to a particular solvent method, the dispersion state of the drug can be obtained by dissolving the drug and the water-soluble polymer in a solvent, and removing the solvent.

The "adhesion of the drug to the water-soluble polymer" includes not only the direct adhesion of the drug to the water-soluble polymer but also the indirect adhesion of the drug to the water-soluble polymer via a binder, etc.

It is preferable that the drug adheres to the surface of the water-soluble polymer (including the case wherein a part of the drug is embedded in the water-soluble polymer, and the other part of the drug is exposed to the outside from the surface of the water-soluble polymer).

The water-soluble polymer to be used for the adhesion of the drug is, in view of the adhesiveness, preferably, one of which viscosity is high (e.g. about 400 cps (400 mpa.s) or more, more preferably about 1000 cps (1000 mpa.s) or more in a 2% aqueous solution).

The viscosity to be used here is kinetic-viscosity, and can be determined by a viscometer such as a Cannon-Fenske viscometer, a Cannon-Fenske viscometer for opaque solution, a Ubbelohde viscometer or Ostwald viscometer. Especially, the determination by Ubbelohde viscometer is preferable in view of the high precision. The viscosity data described in the present specification were determined under the environment at 37° C. using a Ubberohde viscometer manufactured by Shibata Science Machine Industry Co.

The "indirect adhesion via a binder, etc." includes the adhesion of a coating layer comprising the dispersed drug to the surface of the water-soluble polymer carrier. For example, the water-soluble polymer can be used as the coating layer.

In the present preparation, the adhesion of a coating layer comprising the drug dispersed in the water-soluble polymer to the surface of the water-soluble polymer carrier is more preferable than the direct dispersion of the drug to the surface of the water-soluble polymer carrier.

That is, the drug, when dispersed in the water-soluble polymer, exists in the form of monomolecule in the water-soluble polymer, therefore it has a preferably fast solubility rate.

The water-soluble polymer which is used for the coating layer and adheres to the surface of the water-soluble polymer carrier includes the above-exemplified one, and may be the same as or different from the water-soluble polymer to be used as a carrier, but is preferably one which has a low viscosity in view of easier dispersion.

The adhesion of the drug to the water-soluble polymer can be carried out according to an ordinary adhesion method, preferably, for example, according to an adhesion method comprising admixing the drug with the water-soluble polymer (and, if desired, heating), or an adhesion method comprising spraying a solution of the drug in a solvent or a solution of the drug and the water-soluble polymer in a solvent to coat the water-soluble polymer carrier (and, if desired, drying). These methods can be also used in combination.

Herein, the heating is preferably carried out at about 70 to 85° C.

The "solvent to be used for dissolving the drug" refers to a pharmaceutically acceptable solvent such as alcohols or diluents thereof.

Methods for spraying or coating can be carried out by an ordinary method, for example, a method using a pan-coating, a fluidized bed coating apparatus or an airflow drying pan-coating apparatus, or a method using a wet granular such as, for example, a fluidized bed granular (an agitating fluidized bed granular).

The particle size of the drug carried by the water-soluble polymer thus obtained as described above can be adjusted to not more than about 250 μm, if desired, by sieving.

With regard to a weight ratio of the water-soluble polymer to be used for carrying the drug of the present invention to the drug, an amount of the drug is preferably from about 0.001 to about 0.10 part by weight, and especially from about 0.002 to about 0.04 part by weight, per 1 part by weight of the water-soluble polymer.

To the water-soluble polymer which carries the drug of the present invention can be optionally added conventional additives unless the effect of the present invention is degraded, thereby the preparation for nasal administration can be also obtained.

Examples of the conventional additives are perfumes (e.g. menthol), coloring agents, lubricant (e.g. talc, magnesium stearate or a hydrogenated oil) and preservatives (e.g. p-oxybenzoate esters).

In order to avoid the loss of the drug of the present invention before use (e.g. before administration to the nasal cavity), the water-soluble polymer which carries the drug of the present invention (if desired, with additives) is filled into a capsule (hard gelatin capsule) every dosage unit to give an embodiment of the present preparation for nasal administration.

The amount of the effective ingredient in the present preparation is preferably from about 0.05 to about 5% by weight, especially preferably 0.1 to 3% by weight based on the total weight of the preparation.

The present preparation generally can be administered by spraying quantitatively in a form of a solution or a powder (including the powder filled in the hard capsule described above) containing the drug into the nasal cavity by use of a suitable nasal dropper or sprayer (e.g. a device for administration of powder). As a specific example of the administration method, a capsule filled with the powder is placed on a dedicated nasal sprayer with a needle, and run through by the needle, thereby minute holes were made on the upper and lower sides of the capsule, and the powder can be sprayed out therein by taking in air with a rubber ball.

The dose is varied by the age, body weight or conditions of a patient, but it generally is from 1 ng to 1 mg/day per adult as an amount of the effective ingredient.

INDUSTRIAL APPLICABILITY

The present invention makes it possible to provide a preparation for nasal administration which has an excellent sleep-inducing action. Furthermore, the present invention makes it possible to provide a preparation for nasal administration which has not only an elevated bioavailability (hereinafter referred to as "BA") but also a highly direct effect on the brain. Still furthermore, the present invention makes it possible to provide a preparation for nasal administration wherein the prostaglandin is remarkably stable upon storage as shown in the following Experiment 4.

BEST MODE FOR CARRYING OUT THE INVENTION

The present invention is illustrated in more detail by the following examples and experiments, but not limited thereto.

The prostaglandin derivative (herein after referred to as "Drug A") represented by Formula (A) was synthesized according to the method described in Japanese Patent Kokai Hei 7-233144.

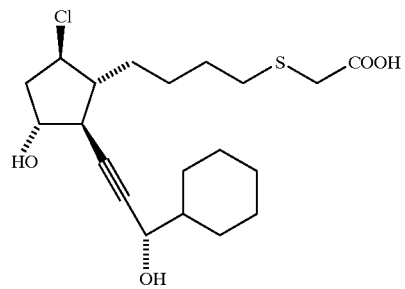

(A)

EXAMPLE 1

With 1 g of hydroxypropyl cellulose (75–250 μm of particle size, 1000–4000 cps of viscosity) was mixed 30 mg of Drug A, followed by heating in a Kjeldahl flask with stirring at 80° C. for 30 minutes. After cooling to room temperature, to this was added 5 mg of magnesium stearate. Then, aliquots of the mixture equivalent to 100 μg and 300 μg of Drug A were filled into capsules to give preparations for nasal administration.

EXAMPLE 2

A solution of 10 mg of Drug A in about 2 ml of ether was mixed little by little with 400 mg of hydroxypropyl cellulose (75–250 μm of particle size, 1000–4000 cps of viscosity), and allowed to stand at room temperature overnight. This was dried at 40° C. for an hour, and sieved for sizing particle (250 μm), followed by addition of 2 mg of magnesium stearate. After mixing in a mix rotor for an hour, each 10.4 mg aliquot was filled into a capsule to give a preparation for nasal administration.

EXAMPLE 3

A solution of 15 mg of Drug A in 2 ml of ethanol was sprayed to 500 mg of hydroxypropyl cellulose (75–250 μm of particle size, 1000–4000 cps of viscosity), coated and dried. To this was added 5 mg of a hydrogenated oil, each 10.4 mg aliquot was filled into a capsule to give a preparation for nasal administration.

EXAMPLE 4

A solution of 20 mg of Drug A in 2 ml of ethanol was sprayed to 500 mg of hydroxypropyl cellulose (75–250 μm of particle size, 1000–4000 cps of viscosity), coated and dried. To this was added 3 mg of magnesium stearate, each 10.4 mg aliquot was filled into a capsule to give a preparation for nasal administration.

EXAMPLE 5

A solution of 15 mg of Drug A and 30 mg of polyvinylpyrrolidone in 2 ml of ethanol was sprayed to 500 mg of hydroxypropyl cellulose (75–250 μm of particle size, 1000–4000 cps of viscosity), coated and dried. To this was added 5 mg of a hydrogenated oil, each 11 mg aliquot was filled into a capsule to give a preparation for nasal administration.

EXAMPLE 6

A solution of 4 g of Drug A in 100 ml of 50% aqueous ethanol solution was sprayed to 400 g of hydroxypropyl cellulose (75–250 μm of particle size, 1000–4000 cps of viscosity) at a spraying rate of 1.5 g/minute by using a agitating fluidized bed granulator (Multiplex, manufactured by Paulex Co.) and dried. After drying, 1 g of magnesium stearate was mixed therewith, each 30 mg aliquot was filled into a capsule to give a preparation for nasal administration.

EXPERIMENT 1 [BA Test by Monkey]

The preparation for nasal administration of Example 1 was nasally administered to a crab-eating monkey by using a device for administration of powder (Jetlizer, Unisiajex Co.). Blood was collected with time, the concentration of Drug A in the plasma was determined by LC/MS/MS. Further, an isotonic phosphate buffer of 100 μg of Drug A was intravenously administered, and the concentration of Drug A in the plasma was also determined with time in the same manner.

From this, there were obtained the area under the drug concentration in blood—time curve (AUC) and bioavailability (BA) (ratio of AUC obtained by nasal administration to AUC obtained by the intravenous administration).

As a result, BA of the preparation for nasal administration of Example 1 was about 70%.

EXPERIMENT 2 [Sleep Test 1 by Monkey]

The preparation for nasal administration (containing 300 μg of Drug A) of Example 1 was nasally administered to a crab-eating monkey by using a device for administration of powder (Jetlizer, Unisiajex Co.). After administration, the monkey was recorded by video, as a result, an accumulated sleep time during 3 hours was 2041 seconds.

Accordingly, the preparation for nasal administration of Example 1 was recognized to have a distinct sleep action.

EXPERIMENT 3 [Sleep Test 2 by Monkey]

The preparation for nasal administration of Example 4 was nasally administered to a crab-eating monkey by using a device for administration of powder (Jetlizer, Unisiajex Co.). After administration, the monkey was recorded by video, and an accumulated sleep time during 3 hours was determined. In a similar manner was determined the sleep time by intravenous administration of an isotonic phosphate buffer of 400 μg of Drug A.

As a result, the accumulated sleep times by the intravenous administration and by the nasal administration of the preparation of Example 4 were 1221 seconds and 3792 seconds, respectively.

That is, even at the same dose, the action by nasal administration is 3 times greater than that by intravenous administration. This result shows that the intracerebral transition rate by the administration of the preparation for nasal administration of Example 4 is higher than that by the intravenous administration.

EXPERIMENT 4 [Stability Test]

Drug A and the preparation for nasal administration of Example 3 were stored at 65° C., and the residual rates of Drug A were quantitatively determined by HPLC with time.

As a result, the residual rates of Drug A were 28.5% and 12.3% after the storage periods for 7 days and 14 days, respectively. On the contrary, the residual rates of Drug A in the preparation of Example 3 were 99.7% and 98.0% after the storage periods for 7 days and 14 days, respectively.

Accordingly, it is found that Drug A by itself has a low residual rate, but Drug A in the preparation of Example 3 has a good stability.

What is claimed is:

1. A preparation for nasal administration which comprises as an effective ingredient a prostaglandin compound represented by Formula (I):

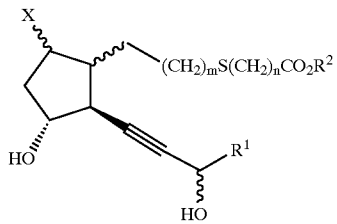

wherein X is a halogen atom, $R^1$ is a $C_{3-10}$ cycloalkyl group, a $C_{3-10}$ cycloalkyl group substituted with $C_{1-4}$ alkyl group(s) or a $C_{4-13}$ cycloalkylalkyl group, $R^2$ is a hydrogen atom, a $C_{1-10}$ alkyl group or a $C_{3-10}$ cycloalkyl group, m is an integer of 0 to 3, and n is an integer of 1 to 4 or a pharmaceutically acceptable salt thereof and a water-soluble polymer, which is at least one member selected from the group consisting of a bridged polyvinyl alcohol, polyvinylpyrrolidone, hydroxypropyl cellulose, a hydroxyalkylmethyl cellulose, hydroxyethyl cellulose, ethylhydroxyethyl cellulose, carboxymethylhydroxyethyl cellulose and cationic cellulose ether.

2. A preparation for nasal administration which comprises as an effective ingredient a prostaglandin compound represented by Formula (A):

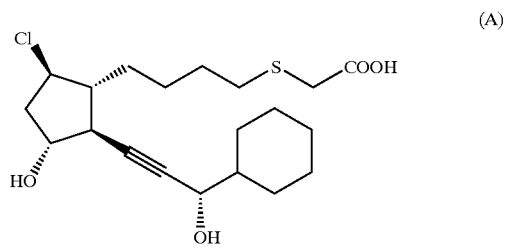

(A)

or a pharmaceutically acceptable salt thereof and a water-soluble polymer, which is at least one member selected from the group consisting of a bridged polyvinyl alcohol, polyvinylpyrrolidone, hydroxypropyl cellulose, a hydroxyalkylmethyl cellulose, hydroxyethyl cellulose, ethylhydroxyethyl cellulose, carboxymethylhydroxyethyl cellulose and cationic cellulose ether.

3. The preparation for nasal administration according to claim 1 or 2 wherein the water-soluble polymer is at least one member selected from the group consisting of hydroxypropyl cellulose, hydroxypropylmethyl cellulose and polyvinylpyrrolidone.

4. The preparation for nasal administration according to claim 1 or 2 wherein the water-soluble polymer is hydroxypropyl cellulose.

5. The preparation for nasal administration according to claim 1 or 2 wherein the water-soluble polymer carries the prostaglandin compound represented by Formula (I) or (A) or the pharmaceutically acceptable salt thereof.

6. The preparation for nasal administration according to claim 5 wherein the prostaglandin compound represented by Formula (I) or (A) or the pharmaceutically acceptable salt thereof adheres to the water-soluble polymer and/or disperses in the water-soluble polymer.

7. The preparation for nasal administration according to claim 5 wherein a coating layer comprising the prostaglandin compound represented by Formula (I) or (A) or the pharmaceutically acceptable salt thereof as an effective ingredient dispersed in the water-soluble polymer, adheres to the surface of the water-soluble polymer for carrying the effective ingredient.

8. A kit of a preparation for nasal administration which comprises the preparation according to claim 1 or 2 and a device for administration.

9. A method for inducing sleep which comprises administering nasally a pharmaceutically effective amount of a sleep-inducing preparation to a human, wherein the sleep-inducing preparation comprises as an effective ingredient a prostaglandin compound represented by Formula (I):

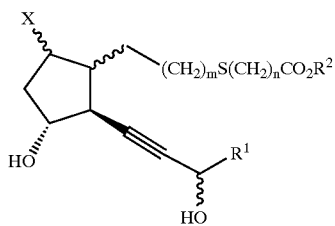

wherein X is a halogen atom, $R^1$ is a $C_{3-10}$ cycloalkyl group, a $C_{1-10}$ cycloalkyl group substituted with $C_{1-4}$ alkyl group(s) or a $C_{4-13}$ cycloalkylalkyl group, $R^2$ is a hydrogen atom, a $C_{1-10}$ alkyl group or a $C_{3-10}$ cycloalkyl group, m is an integer of 0 to 3, and n is an integer of 1 to 4 or a pharmaceutically acceptable salt thereof and a water-soluble polymer.

10. A method for sleep-inducing which comprises administering nasally a pharmaceutically effective amount of a sleep-inducing preparation to a human, wherein the sleep-inducing preparation comprises as an effective ingredient a prostaglandin compound represented by Formula (A):

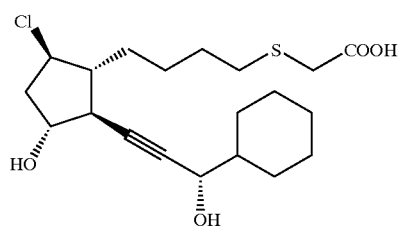

or a pharmaceutically acceptable salt thereof and a water-soluble polymer.

11. The method of claim 9 or 10, wherein the water-soluble polymer is at least one member selected from the group consisting of a bridged vinyl polymer and a water-soluble cellulose ether.

12. The method of claim 9 or 10, wherein the water-soluble polymer is at least one member selected from the group consisting of hydroxypropyl cellulose, hydroxypropylmethyl cellulose, polyvinylpyrrolidone and methyl cellulose.

13. The method of claim 9 or 10, wherein the water-soluble polymer is hydroxypropyl cellulose.

14. The method of claim 9 or 10, wherein the water-soluble polymer carries the prostaglandin compound represented by Formula (I) or (A) or the pharmaceutically acceptable salt thereof.

15. The method of claim 14, wherein the prostaglandin compound represented by Formula (I) or (A) or the pharmaceutically acceptable salt thereof adheres to the water-soluble polymer and/or disperses in the water-soluble polymer.

16. The method of claim 14, wherein a coating layer comprising the prostaglandin compound represented by Formula (I) or (A) or the pharmaceutically acceptable salt thereof as an effective ingredient dispersed in the water-soluble polymer adheres to the surface of the water-soluble polymer for carrying the effective ingredient.

* * * * *